US011655304B2

(12) United States Patent
Lavranos et al.

(10) Patent No.: US 11,655,304 B2
(45) Date of Patent: May 23, 2023

(54) ANTIBODY AND CHECKPOINT INHIBITOR COMBINATION THERAPY

(71) Applicant: Bionomics Limited, Eastwood (AU)

(72) Inventors: Tina Christine Lavranos, Thebarton (AU); Daniel John Inglis, Thebarton (AU); Christopher L. Reyes, Thebarton (AU)

(73) Assignee: Bionomics Limited, Eastwood (AU)

( * ) Notice: Subject to any disclaimer, the term of this patent is extended or adjusted under 35 U.S.C. 154(b) by 197 days.

(21) Appl. No.: 16/333,065

(22) PCT Filed: Sep. 14, 2017

(86) PCT No.: PCT/AU2017/050998
§ 371 (c)(1),
(2) Date: Mar. 13, 2019

(87) PCT Pub. No.: WO2018/049474
PCT Pub. Date: Mar. 22, 2018

(65) Prior Publication Data
US 2019/0263925 A1 Aug. 29, 2019

(30) Foreign Application Priority Data

Sep. 16, 2016 (AU) ................................. 2016903724

(51) Int. Cl.
| | | |
|---|---|---|
| *C07K 16/30* | (2006.01) |
| *A61P 35/00* | (2006.01) |
| *A61K 31/343* | (2006.01) |
| *A61K 31/4741* | (2006.01) |
| *A61K 31/513* | (2006.01) |
| *A61K 31/519* | (2006.01) |
| *A61K 39/395* | (2006.01) |
| *C07K 16/28* | (2006.01) |
| *A61K 45/06* | (2006.01) |
| *A61K 31/661* | (2006.01) |
| *A61K 31/4745* | (2006.01) |
| *A61K 39/00* | (2006.01) |

(52) U.S. Cl.
CPC ............ *C07K 16/30* (2013.01); *A61K 31/343* (2013.01); *A61K 31/4741* (2013.01); *A61K 31/4745* (2013.01); *A61K 31/513* (2013.01); *A61K 31/519* (2013.01); *A61K 31/661* (2013.01); *A61K 39/3955* (2013.01); *A61K 39/39558* (2013.01); *A61K 45/06* (2013.01); *A61P 35/00* (2018.01); *C07K 16/28* (2013.01); *C07K 16/2818* (2013.01); *A61K 2039/505* (2013.01); *A61K 2039/507* (2013.01); *A61K 2039/545* (2013.01); *C07K 2317/21* (2013.01); *C07K 2317/24* (2013.01)

(58) Field of Classification Search
CPC ... A61P 35/00; A61K 31/343; A61K 31/4741; A61K 31/4745; A61K 31/513; A61K 31/519; A61K 39/3955; A61K 39/39558; A61K 2039/505; A61K 2039/507; A61K 2039/545; A61K 45/06; A61K 31/661; A61K 31/513; A61K 31/519; A61K 31/665; A61K 2300/00; C07K 2317/21; C07K 2317/24; C07K 16/30; C07K 16/28; C07K 16/2818
See application file for complete search history.

(56) References Cited

U.S. PATENT DOCUMENTS

| | | | | |
|---|---|---|---|---|
| 9,546,214 B2* | 1/2017 | Reyes | ............... | A61K 39/39558 |
| 10,358,500 B2* | 7/2019 | Reyes | .................... | A61K 45/06 |
| 2015/0166661 A1* | 6/2015 | Chen | .................... | A61K 31/573 |
| | | | | 424/135.1 |
| 2016/0031984 A1* | 2/2016 | Reyes | ............... | A61K 39/39558 |
| | | | | 435/69.6 |
| 2016/0159905 A1* | 6/2016 | Abdiche | .................. | A61P 11/00 |
| | | | | 435/254.2 |
| 2019/0389964 A1* | 12/2019 | Reyes | .................. | A61K 31/519 |
| 2020/0114017 A1* | 4/2020 | Reyes | ................. | A61K 47/6803 |

FOREIGN PATENT DOCUMENTS

| | | |
|---|---|---|
| WO | 2009/005809 A2 | 1/2009 |
| WO | 2013/149159 A1 | 10/2013 |
| WO | 2015/042108 A1 | 3/2015 |
| WO | 2015/153916 A1 | 10/2015 |
| WO | 2015/191715 A1 | 12/2015 |
| WO | 2016/090024 A2 | 6/2016 |
| WO | 2017/040660 A1 | 3/2017 |

OTHER PUBLICATIONS

Allard, B., Pommey, S., Smyth, M. J., & Stagg, J. (2013). Targeting CD73 enhances the antitumor activity of anti-PD-1 and anti-CTLA-4 mAbs. Clinical Cancer Research, 19(20), 5626-5635. (Year: 2013).*
Katsuta, E., Tanaka, S., Mogushi, K., Shimada, S., Akiyama, Y., Aihara, A., . . . & Kudo, A. (2016). CD73 as a therapeutic target for pancreatic neuroendocrine tumor stem cells. International Journal of Oncology, 48(2), 657-669. (Year: 2016).*
Weber, J. S., D'Angelo, S. P., Minor, D., Hodi, F. S., Gutzmer, R., Neyns, B., . . . & Linette, G. P. (2015). The lancet oncology, 16(4), 375-384 (Year: 2015).*
De Lera Ruiz, M., Lim, Y. H., & Zheng, J. (2014). Adenosine A2A receptor as a drug discovery target. Journal of medicinal chemistry, 57(9), 3623-3650. (Year: 2014).*

(Continued)

*Primary Examiner* — Hong Sang
*Assistant Examiner* — Sung Min Yoon
(74) *Attorney, Agent, or Firm* — Nelson Mullins Riley & Scarborough LLP; Jane E. Remillard, Esq.; Jeanne M. DiGiorgio, Esq.

(57) ABSTRACT

The present invention provides a combination therapy for treatment of a tumour in a subject. The combination therapy comprises administration of (i) an antibody directed against cancer stem cells and (ii) a checkpoint inhibitor.

11 Claims, 4 Drawing Sheets

Specification includes a Sequence Listing.

(56) References Cited

OTHER PUBLICATIONS

Pardoll, D. M. (2012). The blockade of immune checkpoints in cancer immunotherapy. Nature Reviews Cancer, 12(4), 252-264. (Year: 2012).*
Ward et al. Nature, 1989, 341:544-546 (Year: 1989).*
Griffiths et al. EMBO Journal, 1993, 12:725-734 (Year: 1993).*
Klimka et al., British Journal of Cancer, 2000, 83:252-260 (Year: 2000).*
Beiboer et al. Journal of Molecular Biology, 2000, 296:833-849 (Year: 2000).*
De Genst et al., Developmental and Comparative Immunology, 2006, 30:187-198 (Year: 2006).*
Barthelemy et al. Journal of Biological Chemistry, 2008, 283:3639-3654 (Year: 2008).*
Choi & Deane, Molecular BioSystems, 2011, 7:3327-3334 (Year: 2011).*
Malia et al., Proteins 2016; 84;427-434 (Year: 2016).*
Guo et al. Nature, 2008, 453(7194):529-533 (Year: 2008).*
Tozer et al. Nature Reviews Cancer 2005, 5:423-435 (Year: 2005).*
Kremmidiotis et al. Mol Cancer Ther 2010, 9(6):1562-1573 (Year: 2010).*
Castle et al. BMC Genomics 2014, 15:190 (Year: 2014).*
Cherciu et al., Current Health Sciences Journal, 2014, 40(3): 153-161 (Year: 2014).*
Lavranos, et al.; Abstract B92: The tubulin-targeting agent BNC105 potentiates the efficacy of immune checkpoint inhibitors in preclinical models of colorectal cancer. Mol Cancer Ther Dec. 1, 2015; 14 (12_Supplement_2): B92. https://doi.org/10.1158/1535-7163.TARG-15-B92 (Year: 2015).*
National Cancer Institute Thesaurus (Version 21.03e, release date Mar. 29, 2021, accessed Apr. 17, 2021, https://ncit.nci.nih.gov/ncitbrowser/pages/home.jsf?version=2 1.03e) (Year: 2021).*
Gong, X. et al. "LGR5-Targeted Antibody-Drug Conjugate Eradicates Gasliointestinal Tumors and Prevents Recurrence," Mol Cancer Ther., vol. 15(7):1580-90 (2016).
Inglis, D.J. et al. "Targeting the LGR5 complex with BNC101 to improve checkpoint inhibitor therapy in colorectal cancer," Cancer Research, vol. 77 (13): 1 page (2017) Supp. Supplement 1. Abrstract No. 4695. Meeting Info: American Association for Cancer Research Annual Meeting 2017. Washington, DC, United States. Apr. 1-5, 2017.
International Preliminary Report on Patentability, PCT/AU2017/050998, dated Mar. 19, 2019, 12 pages.
International Search Report and Written Opinion, PCT/AU2017/050998, dated Nov. 27, 2017, 20 pages.
Pan, Q. et al. "Concise Review: Targeting Cancer Stem Cells Using Immunologic Approaches," Stem Cells, vol. 33 (7):2085-92 (2015).
Deonarain, M. et al., "Antibodies targeting cancer stem cells: A new paradigm in immunotherapy?," mAbs, vol. 1(1): 12-25 (2009).
Junttila, M. et al., "Targeting LGR5+ cells with an antibody-drug conjugate for the treatment of colon cancer," Science Translational Medicine, vol. 7 (314) 314ra186: 10 pages (2015).
Kemper, K. et al., "Monoclonal Antibodies Against Lgr5 Identify Human Colorectal Cancer Stem Cells," Stem Cells, vol. 30:2378-2386 (2012).

* cited by examiner

Figure 1: Tumor Growth inhibition

Figure 2: Total T cell recruitment to the tumor

Figure 3: Cytotoxic T cell recruitment to the tumor

Figure 4: Tumoral Tregs

ANTIBODY AND CHECKPOINT INHIBITOR COMBINATION THERAPY

CROSS-REFERENCE TO RELATED APPLICATIONS

This application is a 35 U.S.C. 371 national stage filing of International Application No. PCT/AU2017/050998, filed Sep. 14, 2017, which claims priority to Australian Application No. 2016903724, filed Sep. 16, 2016. The contents of the aforementioned applications are hereby incorporated by reference.

SEQUENCE LISTING

The instant application contains a Sequence Listing which has been submitted via EFS-Web and is hereby incorporated by reference in its entirety. Said ASCII copy, created on Jul. 28, 2021, is named DAJ_002US_SL.txt and is 6,487 bytes in size.

FIELD OF INVENTION

The present invention relates to a combination therapy for the treatment of tumours. The combination comprises an antibody directed against a cancer stem cell marker and a checkpoint inhibitor.

BACKGROUND OF INVENTION

Currently there is a very strong drive to extend the clinical benefit of immunotherapies to a broader patient population where many patients fail to respond. Immunologic approaches, whereby checkpoint inhibitors are used as a therapy, are biased toward the bulk of the tumor which is comprised of differentiated tumor cells.

Checkpoint inhibitors seek to overcome one of cancer's main defenses against an immune system attack. Immune system T cells patrol the body constantly for signs of disease or infection. When they encounter another cell, they probe certain proteins on its surface, which serve as insignia of the cell's identity. If the proteins indicate the cell is normal and healthy, the T cell leaves it alone. If the proteins suggest the cell is infected or cancerous, the T cell will lead an attack against it. Once T cells initiate an attack, the immune system increases a series of additional molecules to prevent the attack from damaging normal tissues in the body. These molecules are known as immune checkpoints.

Tumor cells often wear proteins that reveal the cells' cancerous nature. But they sometimes commit what amounts to identity theft, arraying themselves in proteins of normal cells. Recent research has shown that cancer cells often utilize immune checkpoint molecules to suppress and evade an immune system attack. T cells, deceived by these normal-looking proteins, may allow the tumor cell to go unmolested.

Checkpoint inhibitors block these normal proteins on cancer cells, or the proteins on T cells that respond to them. The result is to remove the blinders that prevented T cells from recognizing the cells as cancerous and leading an immune system assault on them.

Three checkpoint inhibitors have received rapid approval from the U.S. Food and Drug Administration for cancer, including ipilimumab (Yervoy®), pembrolizumab (Keytruda®), and nivolumab (Opdivo®). These and other immune checkpoint therapies represent one of the most promising frontiers in cancer treatment today.

Cancer stem cells (CSCs) on the other hand display distinct gene and antigen expression profiles compared to this more differentiated tumor bulk. This allows them to evade the therapeutic benefit of checkpoint inhibitors and repopulate tumors. LGR5 has been identified in some solid cancers to be a functional marker of CSCs or tumor initiating subpopulations, which are capable of self-renewal and differentiation into progeny cells lacking these capacities. Significant evidence also indicates that these CSCs have an immunosuppressive phenotype, allowing them to evade the antitumor host immune response [1-8]. This opens the possibility that subsets of CSCs may downregulate T-cell immunity.

The existence of a cell subset within tumours that are able to evade checkpoint inhibitors and downregulate the overall responsiveness to therapy gives scope for a combination therapy with greater therapeutic benefit whereby an anti-LGR5 antibody is combined with checkpoint inhibitors.

The combination of immune checkpoint therapies with CSC targeting agents may improve the clinical utility of each approach and would allow for the high therapeutic value of checkpoint inhibitors to push deeper into patient populations generating a larger number of "responders".

SUMMARY OF INVENTION

The present inventors have determined that a combination of an antibody directed against cancer stem cells and an immunotherapeutic agent increases the efficacy of treating cancer when compared to treatment with either the anti-cancer stem cell antibody or the immunotherapeutic agent alone.

Accordingly, in a first aspect the present invention provides a combination therapy for treating a tumour in a subject, the combination therapy comprising administration of (i) an antibody directed against cancer stem cells and (ii) a checkpoint inhibitor.

In a second aspect the present invention provides a method of treating a tumour in a subject comprising the combination therapy of the present invention.

In a third aspect the present invention provides a composition comprising components (i) and (ii) of the combination therapy in admixture.

In a fourth aspect the present invention provides the use of components (i) and (ii) of the combination therapy in the preparation of a medicament(s) for the treatment of a tumour.

DETAILED DESCRIPTION OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The reference in this specification to any prior publication (or information derived from it), or to any matter which is known, is not, and should not be taken as an acknowledgment or admission or any form of suggestion that prior publication (or information derived from it) or known matter forms part of the common general knowledge in the field of endeavour to which this specification relates.

All publications mentioned in this specification are herein incorporated by reference in their entirety.

It must be noted that, as used in the subject specification, the singular forms "a", "an" and "the" include plural aspects unless the context clearly dictates otherwise. Thus, for example, reference to "an agent" includes a single agent, as well as two or more agents; reference to "a molecule" includes a single molecule, as well as two or more molecules; and so forth.

In a first aspect the present invention provides a combination therapy for treatment of a tumour in a subject, the combination therapy comprising administration of (i) an antibody directed against cancer stem cells and (ii) a checkpoint inhibitor.

In a second aspect the present invention provides a method of treating a tumour in a subject comprising the combination therapy of the present invention.

In a third aspect the present invention provides a composition comprising components (i) and (ii) of the combination therapy in admixture.

In a fourth aspect the present invention provides the use of components (i) and (ii) of the combination therapy in the preparation of a medicament(s) for the treatment of a tumour.

The antibody directed against cancer stem cells is preferably an anti-LGR5 antibody. Examples of such antibodies are described in detail in WO 2015/153916 the disclosure of which is incorporated herein by cross reference.

As mentioned above in a number of embodiments the combination therapy involves use of human or humanized antibodies that specifically bind to LRG5. In some embodiments the antibodies specifically bind LGR5 but do not inhibit R-Spo binding to LGR5. Other embodiments include antibodies that bind LGR5 without inhibiting R-Spo signaling through LGR5. Still other embodiments include antibodies that bind LGR5 but do not inhibit both R-Spo binding or signaling through LGR5. Another embodiment is antibodies that bind LGR5 and also inhibit LGR5 signaling through the Wnt pathway. In some embodiments these antibodies may inhibit LGR5 signaling through the Wnt pathway, and be independent of RSpo signaling.

LGR5 was identified through lineage tracing studies as a highly specific marker of normal stem cells and tumor-initiating cells in the gut. Previously about 150 genes were identified whose expression was quenched following abrogation of Wnt expression. A comprehensive characterization of these 'Wnt target genes' found LGR5 to be selectively expressed on a population of 10-14 proliferating wedge-shaped cells at the crypt base. These crypt-based columnar cells were previously proposed to be a candidate stem cell population. Using in vivo lineage tracing with a heritable lacZ-LGR5 reporter gene, it has been confirmed that LGR5 intestinal stem cells are a multi-potent, self-renewing population of adult intestinal stem cells that give rise to uninterrupted ribbons of lacZ+ progeny cells initiating from the crypt base and extending to the villus tips.

The specific expression of LGR5 on CSCs provides an opportunity to target CSCs selectively and effectively. LGR5 is highly over expressed in CRC, pancreatic and most other solid tumors, compared to normal tissues, thereby providing a wide therapeutic window to target CSCs in CRC, pancreatic, breast, ovarian, lung, gastric and liver cancer.

LGR5 itself is a facultative component of the Wnt-Fzd-LRP receptor complex that binds secreted R-spondin ligands to selectively amplify and enhance Wnt signals on LGR5 positive cells. There is also evidence that LGR5 can signal in a Wnt-independent manner. In addition, the related transmembrane RING-type E3 ubiquitin ligase ZNRF3 (zinc and RING finger 3) or RNF43 (RING finger 43), are uniquely expressed in LGR5+ stem cells and reduce Wnt signals by selectively ubiquitinating frizzled receptors, thereby targeting these Wnt receptors for degradation. The R-spondin ligands interact with LGR5, to form a ternary complex with the transmembrane ZNRF3 or RNF43. Formation of these ternary complexes sequester ZNRF3 or RNF43 from the Wnt-Fzd-LRP complex and stabilize canonical and noncanonical Wnt signaling. Finally, Norrin has been identified as an additional ligand for the LGR family with unknown associated biology.

The gate keeping mutation in CRC is loss of adenomatous polyposis *coli* (APC), resulting in the aberrant activation of Wnt signaling, which normally acts to regulate the balance between stem cell self-renewal and differentiation in the colon crypt. Dysregulated Wnt signaling in intestinal stem cells leads to the formation of adenomatous polyps in the colon that are the precursor to malignant CRC. LGR5 stem cells were confirmed to be the source or root of these mouse intestinal tumors, using a strategy that crossed inducible APC gene knockout mice with mice whose LGR5 stem cells were specifically and randomly labeled with one of four (GFP/YFP/ECFP/RFP) fluorescent genetic markers. The appearance of single colored tumors (i.e., all GFP or all RFP) 4 weeks after induction of APC deletion confirmed that these tumors arose from a single LGR5 stem cell. Furthermore, this model also allowed for the fluorescent genetic tag in the LGR5 stem cells to be flipped to a different color, so that an RFP+ LGR5 cancer stem cell generating a red tumor could be transformed midstream into a ECFP+ LGR5 cancer stem cell, that was still seeding the tumor but now giving rise to blue tumor cells invading the previously all red GFP+ tumor mass. This flipping experiment not only provided further confirmation that LGR5 CSCs are the origin of intestinal tumors, able to initiate and seed the growth of intestinal tumors, but also that they continuously maintain tumor formation (i.e., have long-term repopulating ability).

A functional role of LGR5 in cancer has been validated through ribonucleic acid interference (RNAi) knockdown studies. Knockdown of LGR5 in a panel of CRC tumor cell lines significantly inhibited the growth of soft agar colonies in vitro, and also the growth of HCT116 colon tumor xenografts in vivo. LGR5 RNAi knockdown was subsequently shown to also reduce the growth of CSC colonies from patient-derived CRC tumor cells in vitro. Finally, sorted LGR5+ patient derived xenograft CRC tumor cells were found to be highly tumorigenic in vivo compared to control LGR5-cells.

CSCs are believed to responsible for the high incidence of tumor recurrence in many cancer patients treated with surgery and standard of care chemotherapy. For example, CD44+ CSCs from breast cancer patients were found to be enriched following chemotherapy, and that high levels of CSCs correlated with poor clinical response to chemotherapy. Similarly, in metastatic CRC, LGR5 expression was upregulated in damaged liver following chemotherapy, suggesting that increased LGR5 CSCs in response to chemotherapy initiate and/or acerbate metastatic disease. Indeed, it has been found that LGR5 expression is significantly greater in metastatic sites compared to primary CRC tumors.

Anti-LGR5 Antibodies

As used herein, the term "antibody" includes, but is not limited to, synthetic antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv), Fab fragments, F(ab') fragments, disulfide-linked Fvs (sdFv) (including bi-specific sdFvs), and anti-idiotypic (anti-Id) antibodies, and epitope-binding fragments of any of the above. The antibodies of several embodiments provided herein may be monospecific, bispecific, trispecific or of greater multispecificity. Multispecific antibodies may be specific for different epitopes of a polypeptide or may be specific for both a polypeptide as well as for a heterologous epitope, such as a heterologous polypeptide or solid support material. See, e.g., PCT publications WO93/17715; WO 92/08802; WO91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148: 1547-1553 (1992); each of which is incorporated herein by reference in its entirety.

As used herein, LGR5 includes, but is not limited to, human LGR5 including the polypeptide of NCBI Accession No. NP_003658.1, or fragments thereof, which is encoded by the coding nucleotide sequence within NM_003667.2, or fragments thereof. The amino acid sequence and entire entry of NCBI Accession No. NP_003658.1 and nucleotide sequence and entire entry of NM_003667.2 are fully incorporated by reference in their entireties. Examples of LGR5 fragments contemplated herein include the LGR5 ectodomain, transmembrane domain, or intracellular domain and portions thereof.

WO 2015/15396 discloses hybridomas that produce the light chain and/or the heavy chain of an anti-LGR5 antibody, including the anti-LGR5 antibodies designated as 18G7H6A3 and 18G7H6A1. For human therapy it is preferred that the anti-LGR5 antibody is humanised or human monoclonal antibody. Particular versions of these antibodies are 18G7H6A1 or 18G7H6A3 which are described in WO 2015/153916.

In certain embodiments the antibody comprises a heavy chain CDR1 having amino acids GYSFTAYW (SEQ ID NO:1) or conservative variations thereof.

In certain embodiments the antibody comprises a heavy chain CDR2 having amino acids ILPGSDST (SEQ ID NO:2) or conservative variations thereof.

In certain embodiments the antibody comprises a heavy chain CDR3 having amino acids ARSGYYGSSQY (SEQ ID NO:3) or conservative variations thereof.

In certain embodiments the antibody comprises a light chain CDR1 having amino acids ESVDSYGNSF (SEQ ID NO:4) or conservative variations thereof.

In certain embodiments the antibody comprises a light chain CDR2 having amino acids LTS (SEQ ID NO:5) or conservative variations thereof.

In certain embodiments which the antibody comprises a light chain CDR3 having amino acids QQNAEDPRT (SEQ ID NO:6) or conservative variations thereof.

In certain embodiments the antibody comprises a heavy chain variable domain comprising SEQ ID NOs: 7 or 8.

In certain embodiments the antibody comprises a light chain variable domain comprising SEQ ID NOs: 9 or 10.

In various embodiments, the glycosylation of the antibodies can be modified. For example, an aglycosylated antibody can be made (i.e., the antibody lacks glycosylation). Glycosylation can be altered to, for example, increase the affinity of the antibody for a target antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861; each of which is incorporated herein by reference in its entirety.

In several embodiments, the antibodies specifically bind a polypeptide comprising or consisting of a LGR5 polypeptide having at least 60% identity, or at least 70% identity, or at least 80% identity, at least 85% identity, at least 90% identity, at least 95% identity, or at least at least 97% identity, or at least 99% identity, or 100% identity to the human LGR5 polypeptide of NCBI Accession Nos. NP_003658.1 (SEQ ID NO: 47) or fragments thereof. Such fragments can, for example, be at least about 5, 10, 15, 20, 25, 50, 75, 100, 150, 200, 250, 300, 350, 400, 450, 500, 550, 600, 650, 700, 750, 800, 850, or 900 contiguous or non-contiguous amino acids of the LGR5 polypeptide, or any number of contiguous or non-contiguous amino acids in between any of the aforementioned lengths.

As described above the combination therapy of the present invention involves the use of a check point inhibitor. "Checkpoint inhibitor," as used herein, refers to any compound or agent that inhibits the activity of an immune checkpoint protein. Checkpoint inhibitors can include, but are not limited to, immune checkpoint molecule binding proteins, antibodies (or fragments or variants thereof) that bind to immune checkpoint molecules, nucleic acids that down-regulate expression of the immune checkpoint molecules, or any other molecules that bind to immune checkpoint molecules (i.e. small organic molecules, peptidomimetics, aptamers, etc.) and which inhibit the function and/or activity of the immune checkpoint protein.

In one embodiment, the immune checkpoint inhibitor is selected from an inhibitor of: Programmed Death-Ligand 1 (PD-L1, also known as B7-H1, CD274), Programmed Death 1 (PD-1), CTLA-4, PD-L2 (B7-DC, CD273), LAG3, TIM3, 2B4, A2aR, B7H1, B7H3, B7H4, BTLA, CD2, CD27, CD28, CD30, CD40, CD70, CD80, CD86, CD137, CD160, CD226, CD276, DR3, GALS, GITR, HAVCR2, HVEM, IDO1, IDO2, ICOS (inducible T cell costimulator), KIR, LAIR1, LIGHT, MARCO (macrophage receptor with collageneous structure), PS (phosphatidylserine), OX-40, SLAM, TIGHT, VISTA, and/or VTCN1.

In some embodiments, the immune checkpoint inhibitor is an inhibitor of PD-1. In one embodiment, the immune checkpoint inhibitor is an anti-PD-1 antibody. In one particular embodiment, the immune checkpoint inhibitor is nivolumab. For example, the inhibitors of PD-1 biological activity (or its ligands) disclosed in U.S. Pat. Nos. 7,029,674; 6,808,710; or U.S. Patent Application Nos: 20050250106 and 20050159351 can be used in the methods provided herein. Exemplary antibodies against PD-1 include: Anti-mouse PD-1 antibody Clone J43 (Cat #BE0033-2) from BioXcell; Anti-mouse PD-1 antibody Clone RMP1-14 (Cat #BE0146) from BioXcell; mouse anti-PD-1 antibody Clone EH12; Merck's MK-3475 anti-mouse PD-1 antibody (Keytruda, pembrolizumab, lambrolizumab); and AnaptysBio's anti-PD-1 antibody, known as ANB011; antibody MDX-1 106 (ONO-4538); Bristol-Myers Squibb's human IgG4 monoclonal antibody nivolumab (Opdivo®, BMS-936558, MDX1106); AstraZeneca's AMP-514, and AMP-224; and Pidilizumab (CT-011), CureTech Ltd.

In some embodiments, the immune checkpoint inhibitor is an inhibitor of PD-L1. Exemplary immune checkpoint inhibitors include antibodies (e.g., an anti-PD-L1 antibody), RNAi molecules (e.g., anti-PD-L1 RNAi), antisense molecules (e.g., an anti-PD-L1 antisense RNA), dominant negative proteins (e.g., a dominant negative PD-L1 protein), and small molecule inhibitors. An exemplary anti-PD-L1 antibody includes clone EH12. Exemplary antibodies against PD-L1 include: Genentech's MPDL3280A (RG7446); Anti-mouse PD-L1 antibody Clone 10F.9G2 (Cat #BE0101) from BioXcell; anti-PD-L1 monoclonal antibody MDX-1105 (BMS-936559) and BMS-935559 from Bristol-Meyer's Squibb; MSB0010718C; mouse anti-PD-L1 Clone 29E.2A3; and AstraZeneca's MEDI4736.

In some embodiments, the immune checkpoint inhibitor is an inhibitor of PD-L2. In other embodiments, the immune checkpoint inhibitor reduces the interaction between PD-1 and PD-L2. Exemplary immune checkpoint inhibitors include antibodies (e.g., an anti-PD-L2 antibody), RNAi molecules (e.g., an anti-PD-L2 RNAi), antisense molecules (e.g., an anti-PD-L2 antisense RNA), dominant negative proteins (e.g., a dominant negative PD-L2 protein), and small molecule inhibitors. Antibodies include monoclonal antibodies, humanized antibodies, deimmunized antibodies, and Ig fusion proteins.

In some embodiments, the immune checkpoint inhibitor is an inhibitor of CTLA-4. In one embodiment, the immune checkpoint inhibitor is an anti-CTLA-4 antibody. In one particular embodiment, the immune checkpoint inhibitor is ipilimumab. In one embodiment, the anti-CTLA-4 antibody blocks the binding of CTLA-4 to CD80 (B7-1) and/or CD86 (B7-2) expressed on antigen presenting cells. Exemplary antibodies against CTLA-4 include: Bristol Meyers Squibb's anti-CTLA-4 antibody ipilimumab (also known as Yervoy®, MDX-010, BMS-734016 and MDX-101); anti-CTLA4 Antibody, clone 9H10 from Millipore; Pfizer's tremelimumab (CP-675,206, ticilimumab); and anti-CTLA4 antibody clone BNI3 from Abcam.

In some embodiments, the anti-CTLA-4 antibody is, for example, disclosed in: WO 98/42752; U.S. Pat. Nos. 6,682,736 and 6,207,156; Hurwitz et al. (1998); Camacho et al. (2004) (antibody CP-675206); Mokyr et al. (1998) (incorporated herein by reference).

In some embodiments, the CTLA-4 inhibitor is a CTLA-4 ligand as disclosed in WO1996040915. In some embodiments, the CTLA-4 inhibitor is a nucleic acid inhibitor of CTLA-4 expression.

Any suitable immune checkpoint inhibitor is contemplated for use with the compositions, dosage forms, and methods disclosed herein. The selection of the immune checkpoint inhibitor depends on multiple factors, and the selection of the immune checkpoint inhibitor is within the skills of one of skill in the art. For example, factors to be considered include any additional drug interactions of the immune checkpoint inhibitor, and the length for which the immune checkpoint inhibitor may be taken. In certain instances, the immune checkpoint inhibitor is an immune checkpoint inhibitor which may be taken long-term, for example chronically.

In embodiments where the immune checkpoint inhibitor is an antibody, the antibody may be a monoclonal antibody, synthetic antibody, polyclonal antibody, multispecific antibody (including bi-specific antibodies), human antibody, humanized antibody, chimeric antibody, single-chain Fv (scFv) (including bi-specific scFvs), single chain antibody, Fab fragment, F(ab') fragment, disulfide-linked Fv (sdFv), and epitope-binding fragments of any of the above. In particular, antibodies for use in the present invention include immunoglobulin molecules and immunologically active portions of immunoglobulin molecules, i.e., molecules that contain a binding site for an immune checkpoint molecule that immunospecifically bind to the immune checkpoint molecule. The immunoglobulin molecules for use in the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Preferably, the antibodies for use in the invention are IgG, more preferably, IgG1.

In one embodiment, In addition, immune checkpoint inhibitor may include without limitation humanized or fully human antibodies blocking PD-L1 such as MEDI-4736 (disclosed in WO2011066389 A1), MPDL328 OA (disclosed in U.S. Pat. No. 8,217,149 B2) and MIH1 (Affymetrix obtainable via eBioscience (16.5983.82)) and other PD-L1 inhibitors presently under investigation. According to this invention an immune checkpoint inhibitor is preferably selected from a CTLA-4, PD-1 or PD-L1 inhibitor, such as selected from the known CTLA-4, PD-1 or PD-L1 inhibitors mentioned above (ipilimumab, tremelimumab, labrolizumab, nivolumab, pidilizumab, AMP-244, MEDI-4736, MPDL328 OA, MIH1).

The combination therapy of the present invention will generally be administered as an adjunct to the typical standard of cancer care administered to the patient. Examples of standard chemotherapeutic agents used include cyclophosphamide, methotrexate, 5-fluorouracil, doxorubicin, mustine, vincristine, procarbazine, prednisolone, bleomycin, vinblastine, dacarbazine, etoposide, cisplatin, epirubicin, capecitabine, leucovorin, folinic acid, oxaliplatin, gemcitabine, protein bound paclitaxel and irinotecan. In some instances standard of care will involve the use of a combination of agents such as 5-fluorouracil+leucovorin+irinotecan which is used in the treatment colorectal cancer.

The combination therapy of the present invention may further comprise administration of a vascular disrupting agent (VDA). Information regarding vascular disrupting agents is provided in WO 06/084338, WO 07/087684 and WO 08/070908 the disclosures of which are incorporated herein by reference.

It is preferred that the vascular disrupting agent is a compound of formula (I) or a salt, solvate or prodrug thereof and salts thereof (I)

wherein;
X represents O, S, SO, $SO_2$, Se, SeO, $SeO_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkenyl;

$R^{1C}$ represents $C_{1-3}$ alkoxy, $C_{1-3}$ alkylthio, $C_{1-3}$ alkylamino, or $C_{1-3}$ dialkylamino;

$R^{10}$ represents hydroxy or amino;

L represents C=O, O, S, SO, SO2, Se, SeO, SeO2, C=NZ', or NW where Z' is H, optionally substituted alkyl, optionally substituted aryl or optionally substituted amino; and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

$R^{2A}$-$R^{2E}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of R2A and R2B, R2B and R2C, R2C and R2D, and R2D and R2E, together form an optionally substituted aryl, optionally substituted heterocyclyl, optionally substituted heteroaryl, optionally substituted cycloalkyl, or optionally substituted cycloalkenyl; and Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted aryl, optionally substituted heteroaryl, optionally substituted heterocyclyl, optionally substituted acyl and optionally substituted oxyacyl, or NR'''NR''', where each R''' independently represents H, optionally substituted alkyl, optionally substituted alkenyl, optionally substituted alkynyl, optionally substituted aryl and optionally substituted heteroaryl.

Preferably the vascular disrupting agent is 2-methyl-7-hydroxy-3-(3,4,5-trimethoxybenzoyl)-6-methoxybenzofuran (BNC105) or disodium [6-methoxy-2-methyl-3-(3,4,5-trimethoxybenzoyl)-1-benzofuran-7-yl]phosphate (BNC105P).

The tumour to be treated may be any of a wide range of tumours, however, in certain embodiments the combination therapy is for tumours selected from the group consisting of bladder cancer tumour, breast cancer tumour, colon cancer tumour, gastroenterological cancer tumour, kidney cancer tumour, lung cancer tumour, ovarian cancer tumour, pancreatic cancer tumour, prostate cancer tumour, proximal or distal bile duct cancer tumour, melanoma, colorectal cancer tumour, metastatic colorectal cancer tumour, metastatic pancreatic cancer tumour, triple-negative breast cancer tumour and small cell lung cancer tumour.

EXAMPLES

Example 1. 18G7 (BNC101 Murine Equivalent) in Combination with Anti-PD1

The present inventors conducted a study to determine the efficacy of 18G7 (described in detail in WO 2015/153916)

in combination with the immunotherapeutic anti-PD1 antibody in the syngeneic MC38 murine colon tumor model. 18G7 antibody was administered at 15 mg/kg i.v. on Day 1, 8 and 15, anti-PD1 antibody (Clone RMP1-14) was administered at 5 mg/kg i.p. on Day 1, 4, 8, 12 and 16. C57/BL6 mice were inoculated subcutaneously with MC38 cells. When tumors reached a volume of approximately 100-150 mm$^3$ animals were randomised into groups of 10 mice per group.

Groups:

| Group | N | Treatment | Dose level | Dosing Route | Planned Dosing Schedule/Days | Doses Administered$^a$ |
|---|---|---|---|---|---|---|
| 1 | 15 | PBS | — | i.p. | Day 1, 4, 8, 12, 15, 16 | Day 1, 4, 8, 12, 15, 16, 19 |
| 2 | 15 | Mouse IgG1 isotype | 15 mg/kg | i.p. | Day 1, 8, 15 | Day 1, 8, 15, 19 |
|  |  | Rat IgG2a isotype | 5 mg/kg | i.p. | Day 1, 4, 8, 12, 16 | Day 1, 4, 8, 12, 16, 19 |
| 3 | 15 | 18G7 antibody | 15 mg/kg | i.p. | Day 1, 8, 15 | Day 1, 8, 15, 19 |
|  |  | Rat IgG2a isotype | 5 mg/kg | i.p. | Day 1, 4, 8, 12, 16 | Day 1, 4, 8, 12, 16, 19 |
| 4 | 15 | Mouse IgG1 isotype | 15 mg/kg | i.p. | Day 1, 8, 15 | Day 1, 8, 15, 19 |
|  |  | Anti-PD-1 | 5 mg/kg | i.p. | Day 1, 4, 8, 12, 16 | Day 1, 4, 8, 12, 16, 19 |
| 5 | 15 | 18G7 antibody | 15 mg/kg | i.p. | Day 1, 8, 15 | Day 1, 8, 15, 19 |
|  |  | Anti-PD-1 | 5 mg/kg | i.p. | Day 1, 4, 8, 12, 16 | Day 1, 4, 8, 12, 16, 19 |

The objective of this study was to evaluate pre-clinically the in vivo therapeutic efficacy of the 18G7 antibody as a single agent or in combination with anti-PD-1 antibody in the treatment of subcutaneous MC38 mouse colon adenocarcinoma model in C57BL/6 immuno-competent mice. This syngeneic model is known to be responsive to anti-PD-1 monotherapy, allowing for an additive/synergistic effect to be seen from complementary therapies in a traditional tumor growth inhibition study. The expectations from cancer stem cell (CSC) targeting agents however is that a direct TGI effect will not necessarily be seen in a short term study, more so that the treatments will prime the tumor and the immune system for long term benefit after standard of care chemotherapy or surgery extending the duration of response. The current study points to this being the case.

Figure 1:
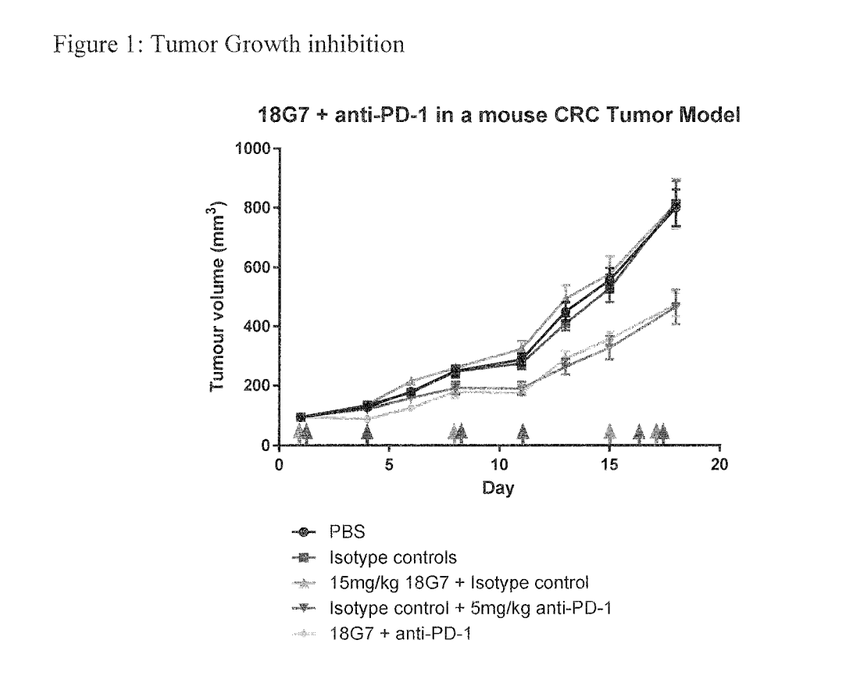
FIG. 1. Tumour growth inhibition in a mouse colorectal cancer (CRC) tumor model

In FIG. 1 the tumor growth inhibition graph shows that the anti PD-1 was the effector in terms of growth inhibition as expected from the MC38 model. No additional benefit was drawn from LGR5 inhibition by the 18G7 antibody in this experimental format looking solely at tumor growth inhibition over 18 days. MC38 cells are known to express LGR5 however binding of the 18G7 antibody to the cells has not lead to a direct anti-proliferative effect.

CSCs are known to have an immunosuppressive ability on the tumor microenvironment, dampening an immune attack on the tumor. Ideally a reduction in LGR5+ve CSCs by BNC101 treatment, would limit their immunosuppressive ability allowing greater therapeutic activity of anti-PD-1. This is an effect that may take longer to be seen than the ethical limits of this animal model allows or have to be demonstrated in a re-implantation assay.

With these limitations taken in to consideration, flow cytometric analysis of the tumors does allow a snapshot of effector immune cells with population changes pointing toward a change which may not have had the opportunity to play out at the early time frame of 18 days, (albeit anti-PD-1 has had activity in this time, through its assumed mechanism of action whereby cytotoxic T cells remain viable against the tumor target). Flow cytometry was conducted on the samples at termination (Day 20). Tumors were analysed for the following populations: CD3, CD4, CD8; CD4, CD25, Foxp3 and CD11b, Ly6G, Ly6C.

Figure 2:
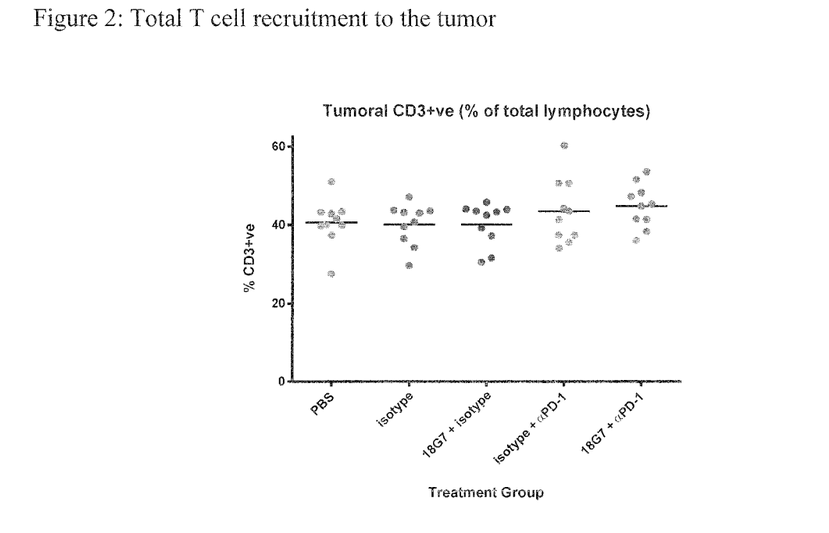
FIG. 2. Total T cell recruitment to the tumor-tumoral $CD3^+$ as a % of total lymphocytes FIG. 3. Cytotoxic T cell recruitment to the tumor-tumoral $CD8^+$ as a % of CD3

Total T cell (CD3+ve) recruitment to the tumor remains relatively stable across treatments although small non-significant increases in T cell content can be seen in the tumors from anti-PD-1 treated animals consistent with the treatment maintaining/expanding CD8 cells (a subset of CD3) (FIG. 2).

Figure 3:
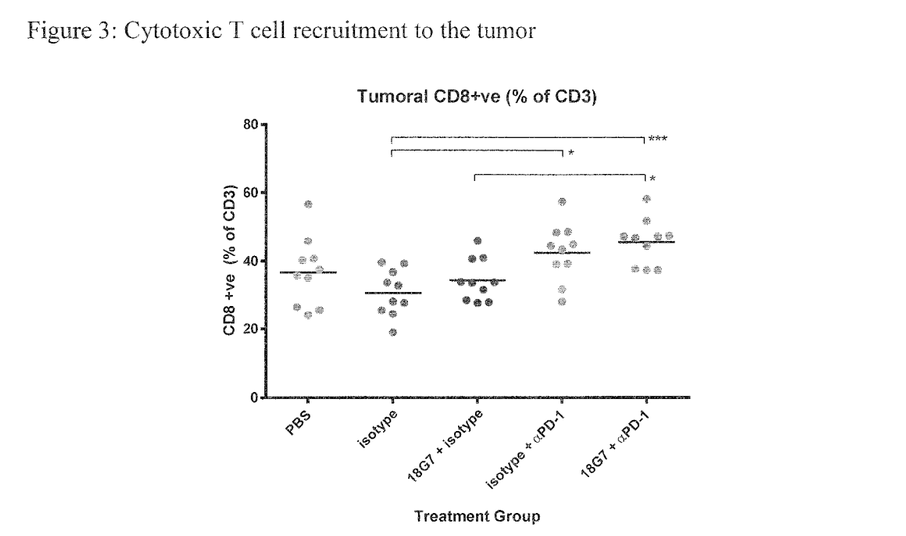

The significant increase in tumor based cytotoxic T cells is evident in the anti-PD-1 treated animals, and most interestingly further increased by the addition of 18G7. Although the comparison between anti-PD-1 and anti-PD-1+18G7 is not significant, a further increase in significance compared to isotype exemplifies an effect consistent with the premise that a reduction in immunosuppressive CSCs allows for a greater accumulation of cytotoxic T cells—a further "taking the brakes off the immune system" (FIG. 3). Other tumor microenvironment factors caused by anti-LGR5 targeting of the LGR5 expressing tumor bulk and not just CSC's alone may add to this effect.

The analysis of tumoral Treg cells is perhaps the most promising of the results. Regulatory T cells (CD4+/CD25+/FoxP3+) or suppressor cells generally suppress or down-regulate local activation of the immune system and prevent pathological self-reactivity. In the context of cancer this translates to immune dampening and immune-avoidance by tumors suppressing the induction and proliferation of cytotoxic CD8 cells.

Figure 4:
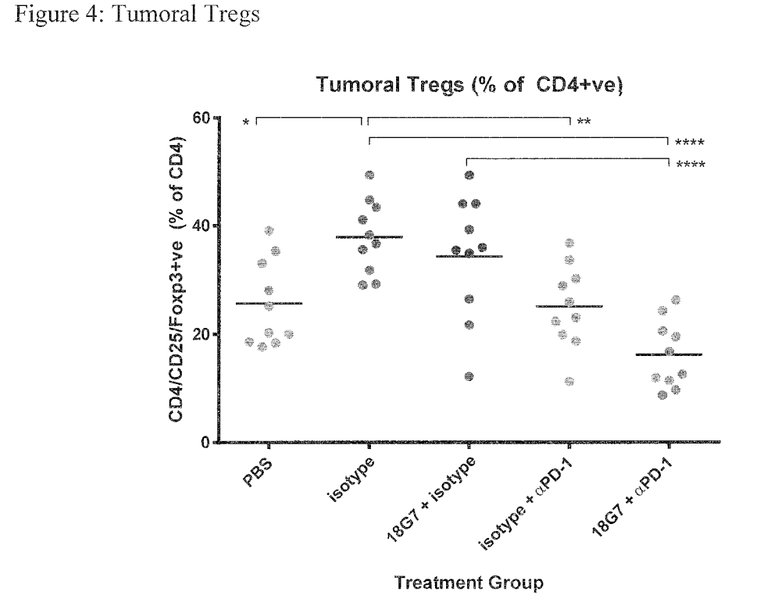
FIG. 4. Tumoral Tregs as % of $CD4^+$

The complex signalling pathway alliance between CSCs and immune suppression via Tregs is seen in the literature and potentially pointed to here. Compared to isotype control there is a reduction in Tregs from 18G7 treatment (9.4%), a significant reduction in Tregs when anti-PD-1 monotherapy is used (33.9% reduction) but an even more significant decrease in Tregs when it is used in combination with 18G7 (57.3% reduction) (FIG. 4). This result could be key understanding a place for anti-LGR5 antibody therapy within the immunotherapeutic combination field.

Sequence ID Listing

| Description | SEQ ID NO: |
|---|---|
| Heavy Chain CDR1 | 1 |
| Heavy Chain CDR2 | 2 |
| Heavy Chain CDR3 | 3 |
| Light Chain CDR1 | 4 |
| Light Chain CDR2 | 5 |
| Light Chain CDR3 | 6 |
| Heavy Chain Variable Domain | 7 |
| Light Chain Variable Domain | 8 |
| Heavy Chain Variable Domain | 9 |
| Light Chain Variable Domain | 10 |

REFERENCES

1. Lee Y, Sunwoo J. PD-L1 is preferentially expressed on CD44+ tumor-initiating cells in head and neck squamous cell carcinoma. Journal for Immunotherapy of Cancer. 2014; 2 (Suppl 3):P270. doi:10.1186/2051-1426-2-S3-P270.
2. Hanahan D, Coussens L M. Accessories to the crime: functions of cells recruited to the tumor microenvironment. Cancer Cell. 2012; 21:309-322. [PubMed]
3. Galon J, Costes A, Sanchez-Cabo F, Kirilovsky A, Mlecnik B, Lagorce-Pagès C, Tosolini M, Camus M, Berger A, Wind P, et al. Type, density, and location of immune cells within human colorectal tumors predict clinical outcome. Science. 2006; 313:1960-1964. [PubMed]
4. Zindl C L, Chaplin D D. Immunology. Tumor immune evasion. Science. 2010; 328:697-698. [PubMed]
5. Schatton T, Schütte U, Frank N Y, Zhan Q, Hoerning A, Robles S C, Zhou J, Hodi F S, Spagnoli G C, Murphy G F, et al. Modulation of T-cell activation by malignant melanoma initiating cells. Cancer Res. 2010; 70:697-708. [PubMed]
6. Wei J, Barr J, Kong L Y, Wang Y, Wu A, Sharma A K, Gumin J, Henry V, Colman H, Sawaya R, et al. Glioma-associated cancer-initiating cells induce immunosuppression. Clin Cancer Res. 2010; 16:461-473. [PubMed]
7. Wei J, Barr J, Kong L Y, Wang Y, Wu A, Sharma A K, Gumin J, Henry V, Colman H, Priebe W, et al. Glioblastoma cancer-initiating cells inhibit T-cell proliferation and effector responses by the signal transducers and activators of transcription 3 pathway. Mol Cancer Ther. 2010; 9:67-78. [PubMed]
8. Kryczek I, Lin Y, Nagarsheth N, Peng D, Zhao L, Zhao E, Vatan L, Szeliga W, Dou Y, Owens S, et al. IL-22(+) CD4(+) T cells promote colorectal cancer stemness via STAT3 transcription factor activation and induction of the methyltransferase DOT1L. Immunity. 2014; 40:772-784. [PubMed]

The invention claimed is:

1. A method of treating a colorectal tumour in a subject, wherein the tumor comprises cancer stem cells that express LGR5, the method comprising a combination therapy comprising administration of (i) an antibody directed against leucine-rich repeat containing G-protein-coupled receptor 5 (LGR5), wherein the antibody comprises a heavy chain CDR1 having amino acids GYSFTAYW (SEQ ID NO:1), a heavy chain CDR2 having amino acids ILPGSDST (SEQ ID NO:2), a heavy chain CDR3 having amino acids ARSGYYGSSQY (SEQ ID NO:3), a light chain CDR1 having amino acids ESVDSYGNSF (SEQ ID NO:4), a light chain CDR2 having amino acids LTS (SEQ ID NO:5), and a light chain CDR3 having amino acids QQNAEDPRT (SEQ ID NO:6), and (ii) a checkpoint inhibitor, wherein the inhibitor is an antibody that binds to PD-1.

2. The method as claimed in claim 1 in which the antibody comprises a heavy chain variable domain comprising SEQ ID NOs: 7 or 8.

3. The method as claimed in claim 1 in which the antibody comprises a light chain variable domain comprising SEQ ID NOs: 9 or 10.

4. The method as claimed in claim 1 in which the antibody that binds to PD-1 is selected from the group consisting of pembrolizumab, nivolumab and combinations thereof.

5. The method as claimed in claim 1 in which the combination therapy is administered in conjunction with standard of cancer care.

6. The method as claimed in claim 5 in which standard of cancer care comprises administration of a chemotherapeutic agent or combination of chemotherapeutic agents.

7. The method as claimed in claim 6 in which the chemotherapeutic agent is selected from the group consisting of cyclophosphamide, methotrexate, 5-fluorouracil, doxorubicin, mustine, vincristine, procarbazine, prednisolone, bleomycin, vinblastine, dacarbazine, etoposide, cisplatin, epirubicin, capecitabine, leucovorin, folinic acid, oxaliplatin, gemcitabine, protein bound paclitaxel, irinotecan and combinations thereof.

8. The method as claimed in claim 6 in which the standard of care comprises 5-fluorouracil+leucovorin+irinotecan.

9. The method as claimed in claim 6 wherein the chemotherapeutic agent is a vascular disrupting agent.

10. The method as claimed in claim 9 wherein the vascular disrupting agent is 2-methyl-7-hydroxy-3-(3,4,5-trimethoxybenzoyl)-6-methoxybenzofuran (BNC105) or disodium [6-methoxy-2-methyl-3-(3,4,5-trimethoxybenzoyl)-1-benzofuran-7-yl] phosphate (BNC105P).

11. The method as claimed in claim 1 wherein the colorectal tumour is metastatic colorectal cancer tumour.

* * * * *

```
                        SEQUENCE LISTING

<160> NUMBER OF SEQ ID NOS: 10

<210> SEQ ID NO 1
<211> LENGTH: 8
<212> TYPE: PRT
<213> ORGANISM: Artificial Sequence
<220> FEATURE:
<223> OTHER INFORMATION: Heavy Chain CDR1

<400> SEQUENCE: 1

Gly Tyr Ser Phe Thr Ala Tyr Trp
1               5

<210> SEQ ID NO 2
<211> LENGTH: 8
<212> TYPE: PRT
<213> ORGANISM: Artificial Sequence
<220> FEATURE:
<223> OTHER INFORMATION: Heavy Chain CDR2

<400> SEQUENCE: 2

Ile Leu Pro Gly Ser Asp Ser Thr
1               5

<210> SEQ ID NO 3
<211> LENGTH: 11
<212> TYPE: PRT
<213> ORGANISM: Artificial Sequence
<220> FEATURE:
<223> OTHER INFORMATION: Heavy Chain CDR3

<400> SEQUENCE: 3

Ala Arg Ser Gly Tyr Tyr Gly Ser Ser Gln Tyr
1               5                   10

<210> SEQ ID NO 4
<211> LENGTH: 10
<212> TYPE: PRT
```

```
<213> ORGANISM: Artificial Sequence
<220> FEATURE:
<223> OTHER INFORMATION: Light Chain CDR1

<400> SEQUENCE: 4

Glu Ser Val Asp Ser Tyr Gly Asn Ser Phe
1               5                   10

<210> SEQ ID NO 5
<211> LENGTH: 3
<212> TYPE: PRT
<213> ORGANISM: Artificial Sequence
<220> FEATURE:
<223> OTHER INFORMATION: Light Chain CDR2

<400> SEQUENCE: 5

Leu Thr Ser
1

<210> SEQ ID NO 6
<211> LENGTH: 9
<212> TYPE: PRT
<213> ORGANISM: Artificial Sequence
<220> FEATURE:
<223> OTHER INFORMATION: Light Chain CDR3

<400> SEQUENCE: 6

Gln Gln Asn Ala Glu Asp Pro Arg Thr
1               5

<210> SEQ ID NO 7
<211> LENGTH: 137
<212> TYPE: PRT
<213> ORGANISM: Artificial Sequence
<220> FEATURE:
<223> OTHER INFORMATION: Heavy Chain Variable Domain

<400> SEQUENCE: 7

Met Glu Trp Ser Trp Val Phe Leu Phe Phe Leu Ser Val Thr Thr Gly
1               5                   10                  15

Val His Ser Glu Val Gln Leu Val Gln Ser Gly Ala Glu Val Lys Lys
            20                  25                  30

Pro Gly Glu Ser Leu Arg Ile Ser Cys Lys Gly Ser Gly Tyr Ser Phe
        35                  40                  45

Thr Ala Tyr Trp Ile Glu Trp Val Arg Gln Ala Pro Gly Lys Gly Leu
    50                  55                  60

Glu Trp Ile Gly Glu Ile Leu Pro Gly Ser Asp Ser Thr Asn Tyr Asn
65                  70                  75                  80

Glu Lys Phe Lys Gly His Val Thr Ile Ser Ala Asp Lys Ser Ile Ser
                85                  90                  95

Thr Ala Tyr Leu Gln Trp Ser Ser Leu Lys Ala Ser Asp Thr Ala Val
            100                 105                 110

Tyr Tyr Cys Ala Arg Ser Gly Tyr Gly Ser Ser Gln Tyr Trp Gly
        115                 120                 125

Gln Gly Thr Leu Val Thr Val Ser Ser
    130                 135

<210> SEQ ID NO 8
<211> LENGTH: 137
<212> TYPE: PRT
<213> ORGANISM: Artificial Sequence
<220> FEATURE:
<223> OTHER INFORMATION: Heavy Chain Variable Domain
```

```
<400> SEQUENCE: 8

Met Glu Trp Ser Trp Val Phe Leu Phe Phe Leu Ser Val Thr Thr Gly
1               5                   10                  15

Val His Ser Glu Val Gln Leu Val Gln Ser Gly Ala Glu Val Lys Lys
            20                  25                  30

Pro Gly Glu Ser Leu Arg Ile Ser Cys Lys Gly Ser Gly Tyr Ser Phe
        35                  40                  45

Thr Ala Tyr Trp Ile Glu Trp Val Arg Gln Ala Pro Gly Lys Gly Leu
    50                  55                  60

Glu Trp Ile Gly Glu Ile Leu Pro Gly Ser Asp Ser Thr Asn Tyr Asn
65                  70                  75                  80

Glu Lys Phe Lys Gly His Val Thr Ile Ser Ala Asp Lys Ser Ile Ser
                85                  90                  95

Thr Ala Tyr Leu Gln Trp Ser Ser Leu Lys Ala Ser Asp Thr Ala Val
            100                 105                 110

Tyr Tyr Cys Ala Arg Ser Gly Tyr Gly Ser Ser Gln Tyr Trp Gly
        115                 120                 125

Gln Gly Thr Leu Val Thr Val Ser Ser
    130                 135

<210> SEQ ID NO 9
<211> LENGTH: 131
<212> TYPE: PRT
<213> ORGANISM: Artificial Sequence
<220> FEATURE:
<223> OTHER INFORMATION: Light Chain Variable Domain

<400> SEQUENCE: 9

Met Ser Val Pro Thr Gln Val Leu Gly Leu Leu Leu Leu Trp Leu Thr
1               5                   10                  15

Asp Ala Arg Cys Asp Ile Val Leu Thr Gln Ser Pro Ala Ser Leu Ala
            20                  25                  30

Val Ser Pro Gly Gln Arg Ala Thr Ile Thr Cys Arg Ala Ser Glu Ser
        35                  40                  45

Val Asp Ser Tyr Gly Asn Ser Phe Met His Trp Tyr Gln Gln Lys Pro
    50                  55                  60

Gly Gln Pro Pro Lys Leu Leu Ile Tyr Leu Thr Ser Asn Leu Glu Ser
65                  70                  75                  80

Gly Val Pro Asp Arg Phe Ser Gly Ser Gly Ser Gly Thr Asp Phe Thr
                85                  90                  95

Leu Thr Ile Asn Pro Val Glu Ala Asn Asp Ala Ala Thr Tyr Tyr Cys
            100                 105                 110

Gln Gln Asn Ala Glu Asp Pro Arg Thr Phe Gly Gly Gly Thr Lys Leu
        115                 120                 125

Glu Ile Lys
    130

<210> SEQ ID NO 10
<211> LENGTH: 131
<212> TYPE: PRT
<213> ORGANISM: Artificial Sequence
<220> FEATURE:
<223> OTHER INFORMATION: Light Chain Variable Domain

<400> SEQUENCE: 10

Met Ser Val Pro Thr Gln Val Leu Gly Leu Leu Leu Leu Trp Leu Thr
1               5                   10                  15
```

```
Asp Ala Arg Cys Asp Ile Val Leu Thr Gln Ser Pro Ala Ser Leu Ala
            20                  25              30

Val Ser Pro Gly Gln Arg Ala Thr Ile Thr Cys Arg Ala Ser Glu Ser
        35              40              45

Val Asp Ser Tyr Gly Asn Ser Phe Met His Trp Tyr Gln Gln Lys Pro
    50              55                  60

Gly Gln Pro Pro Lys Leu Leu Ile Tyr Leu Thr Ser Asn Leu Glu Ser
65              70                  75                      80

Gly Val Pro Asp Arg Phe Ser Gly Ser Gly Ser Gly Thr Asp Phe Thr
                85              90              95

Leu Thr Ile Asn Pro Val Glu Ala Asn Asp Ala Ala Thr Tyr Tyr Cys
            100             105             110

Gln Gln Asn Ala Glu Asp Pro Arg Thr Phe Gly Gly Gly Thr Lys Leu
        115             120             125

Glu Ile Lys
    130
```